United States Patent
Jones et al.

(10) Patent No.: US 7,927,348 B2
(45) Date of Patent: *Apr. 19, 2011

(54) STRETCH RESISTANT COIL DEVICE

(75) Inventors: Donald K Jones, Dripping Springs, TX (US); Vladimir Mitelberg, Austin, TX (US)

(73) Assignee: Codman & Shurtleff, Inc., Raynham, MA (US)

( * ) Notice: Subject to any disclaimer, the term of this patent is extended or adjusted under 35 U.S.C. 154(b) by 209 days.

This patent is subject to a terminal disclaimer.

(21) Appl. No.: 11/539,937

(22) Filed: Oct. 10, 2006

(65) Prior Publication Data

US 2008/0086217 A1    Apr. 10, 2008

(51) Int. Cl.
*A61M 29/00* (2006.01)
(52) U.S. Cl. .............. 606/200; 606/191; 623/23.76
(58) Field of Classification Search ............. 606/200; 623/1.15, 23.76
See application file for complete search history.

(56) References Cited

U.S. PATENT DOCUMENTS

| | | | |
|---|---|---|---|
| 5,217,484 A | 6/1993 | Marks | |
| 5,261,916 A | 11/1993 | Engelson | |
| 5,304,195 A | 4/1994 | Twyford, Jr. et al. | |
| 5,582,619 A * | 12/1996 | Ken | 606/191 |
| 5,833,705 A | 11/1998 | Ken et al. | |
| 5,853,418 A | 12/1998 | Ken et al. | |
| 6,004,338 A | 12/1999 | Ken et al. | |
| 6,013,084 A | 1/2000 | Ken et al. | |
| 6,063,100 A | 5/2000 | Diaz et al. | |
| 6,117,157 A * | 9/2000 | Tekulve | 606/200 |
| 6,179,857 B1 | 1/2001 | Diaz et al. | |
| 6,183,491 B1 * | 2/2001 | Lulo | 606/191 |
| 6,193,728 B1 * | 2/2001 | Ken et al. | 606/108 |
| 6,551,340 B1 | 4/2003 | Konya et al. | |
| 6,616,617 B1 * | 9/2003 | Ferrera et al. | 600/585 |
| 2003/0014073 A1 | 1/2003 | Bashiri et al. | |
| 2003/0120302 A1 * | 6/2003 | Minck et al. | 606/200 |
| 2004/0002733 A1 * | 1/2004 | Teoh | 606/200 |
| 2004/0034378 A1 * | 2/2004 | Monstadt et al. | 606/157 |
| 2005/0043755 A1 | 2/2005 | Wilson et al. | |
| 2006/0079926 A1 | 4/2006 | Desai et al. | |

FOREIGN PATENT DOCUMENTS

WO    WO 2006/032291 A1    3/2006

OTHER PUBLICATIONS

European Search Report dated Dec. 12, 2007 for European Application No. EP 07 25 3738.

* cited by examiner

*Primary Examiner* — (Jackie) Tan-Uyen T Ho
*Assistant Examiner* — Julie A Szpira

(57) ABSTRACT

A coil device is provided with a stretch resistant feature. The device includes a wound coil defining a lumen and a stretch resistant member at least partially received within the lumen. A restrictor member is also at least partially received within the lumen and defines an aperture adapted to movably receive a portion of the stretch resistant member to allow the wound coil to stretch and elongate. The stretch resistant member includes an enlarged portion that is larger than the aperture and adapted to engage the restrictor member to prevent or resist stretching of the wound coil. The restrictor member may be provided as a separate element fixedly secured to the coil wire, or the coil wire may include one or more minor turns adapted to perform the function of the restrictor member.

23 Claims, 3 Drawing Sheets

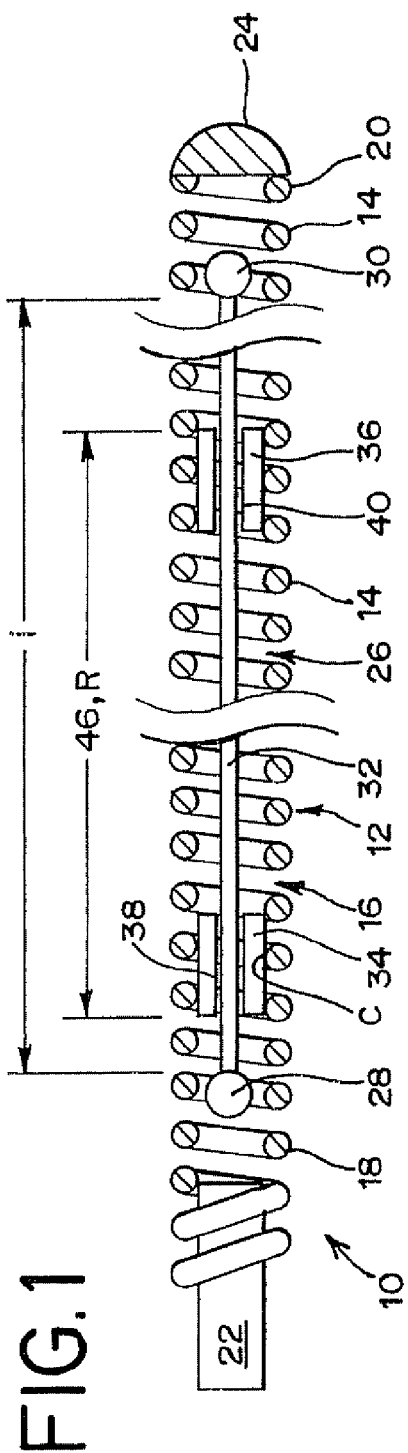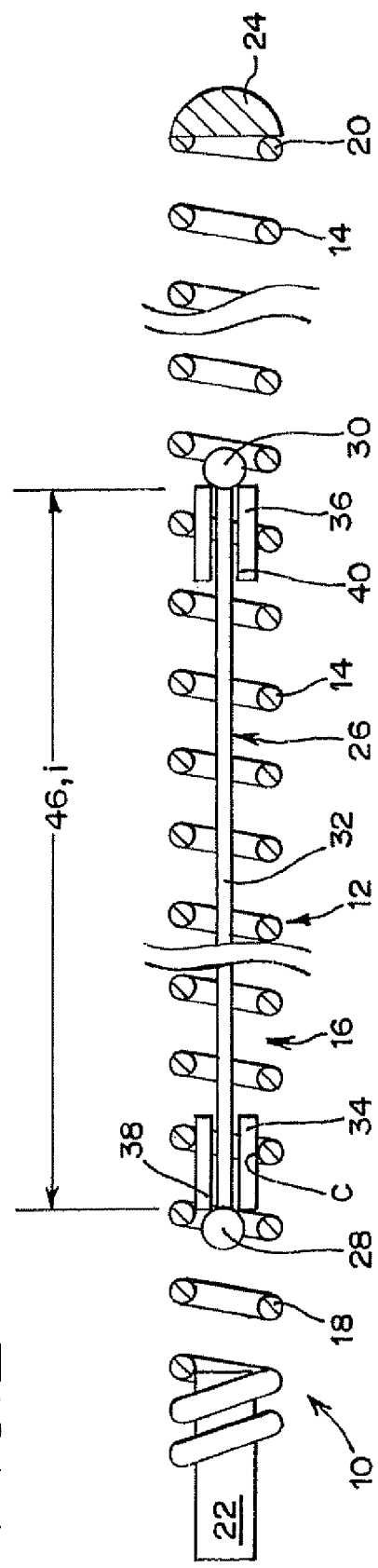

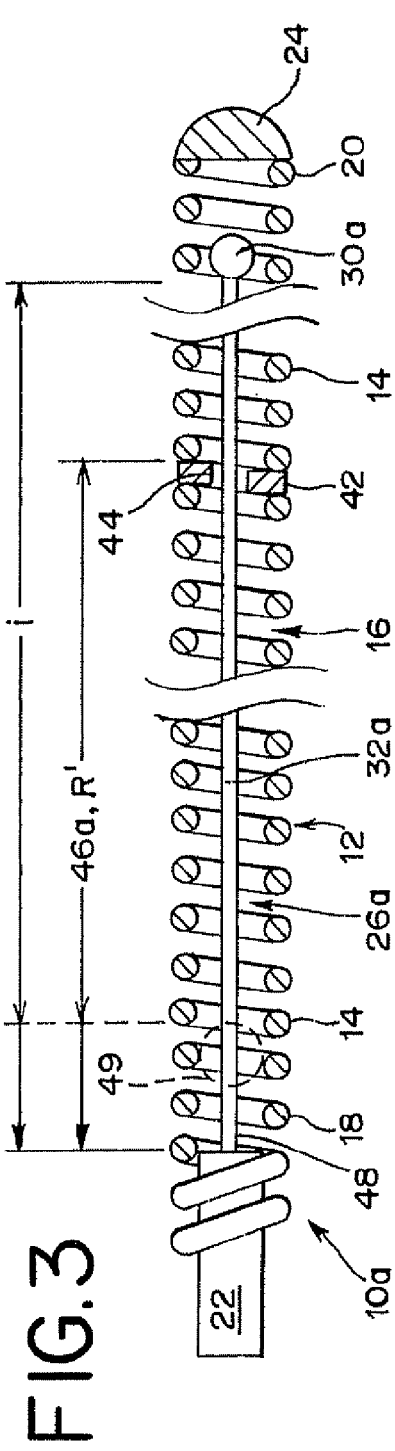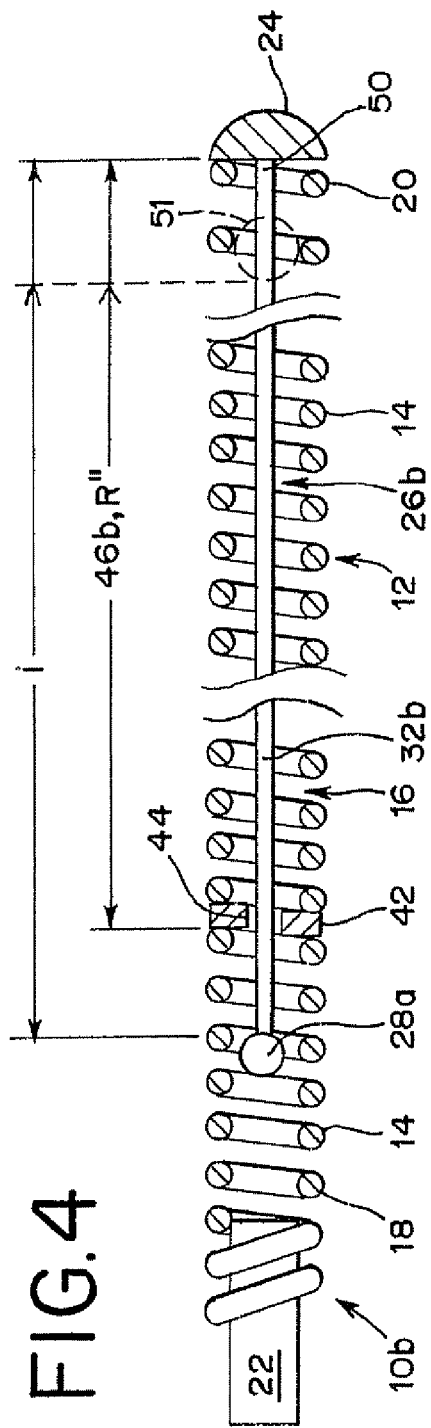

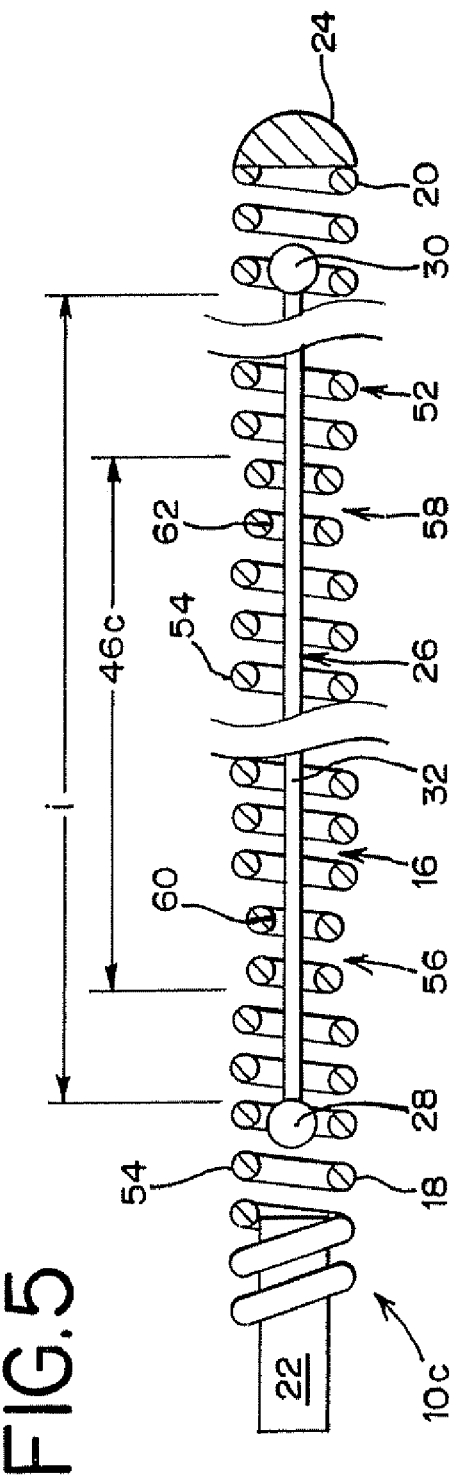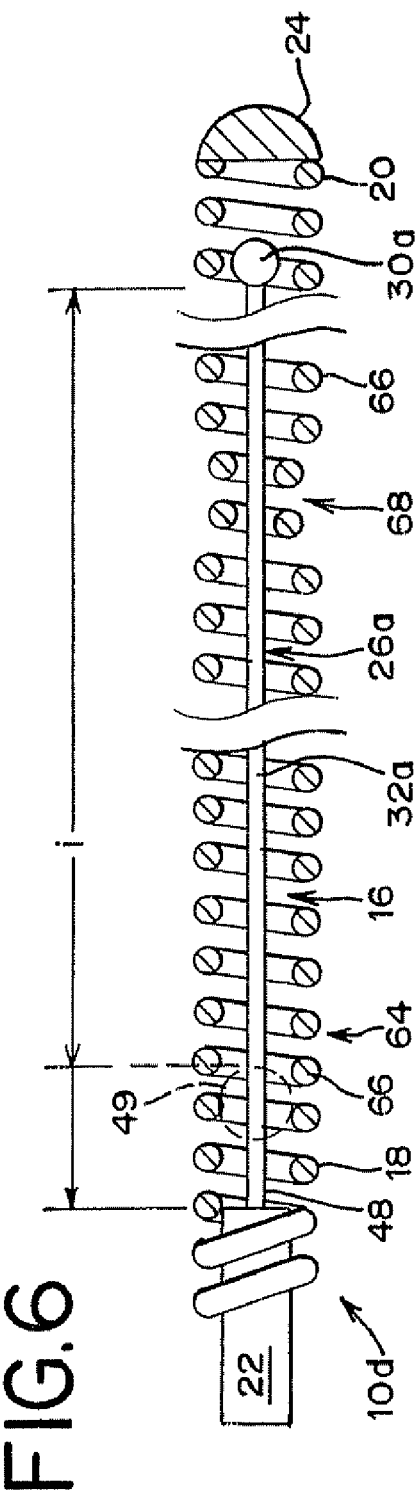

STRETCH RESISTANT COIL DEVICE

FIELD OF THE INVENTION

This invention generally relates to medical devices implantable within body vessels and vessel defects of a human subject. More particularly, this invention relates to embolic coils having a stretch resistant feature

DESCRIPTION OF RELATED ART

The use of embolic coils in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat defects of the cranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site, such as an aneurysm. A vascular occlusion device, such as an embolic coil, is attached to the end of a delivery member, which pushes the coil through the catheter and out of the distal end of the catheter into the delivery site. A multiplicity of coils can be packed within the aneurysm to limit or prevent blood flow thereinto. Some of the problems that have been associated with these procedures relate to stretching of the embolic coils. For example, a stretched coil may exhibit diminished pushability and/or retractability. Furthermore, an overly stretched coil will occupy less volume than a relaxed or un-stretched coil, thereby occupying less space within an aneurysm, which increases the number of coils required to sufficiently pack the aneurysm and prevent blood flow thereinto In response to these concerns, devices have been developed in an attempt to provide a coil that will resist stretching. One such device is disclosed in U.S. Pat. No. 5,582,619 to Ken, which is hereby incorporated herein by reference. The coils described in Ken include an elongated stretch-resisting member received within the lumen of the coil and fixed at each end of the coil. The stretch-resisting member prevents excessive stretching, but may adversely affect the flexibility of the coil because it extends along the entire length of the coil. It is important for embolic coils to be flexible, because they must adapt to the shape of the target site and any other previously placed coils.

One approach to the flexibility concerns associated with the Ken coils is described in U.S. Pat. No. 6,183,491 to Lulo, which is hereby incorporated herein by reference. Lulo provides a coil with a support wire fixedly attached to a proximal end of the coil and to an intermediate portion of the coil, proximal to the distal end of the coil. Hence, the Lulo coil is proposed for preventing stretching of the turns of the coil between the ends of the support wire by tightly securing them to each other. However, it may be desirable to allow for some limited stretching of the turns of the coil between the ends of the support wire for increased flexibility Therefore, a need remains for an embolic coil having an optimal combination of stretch resistance and flexibility.

SUMMARY OF THE INVENTION

In accordance with one embodiment or aspect of the present invention, an embolic coil is provided with a wound coil having a plurality of turns defining a lumen. The embolic coil further includes a stretch resistant member at least partially received within the lumen and having a proximal end, a distal end, a proximal enlarged portion, and a distal enlarged portion. Proximal and distal restrictor members are also at least partially received within the lumen, wherein the proximal restrictor member defines an aperture smaller than the proximal enlarged portion, and the distal restrictor member defines an aperture smaller than the distal enlarged portion. A portion of the stretch resistant member is movable through the apertures to allow stretching of the wound coil until the proximal enlarged portion engages the proximal restrictor member and the distal enlarged portion engages the distal restrictor member to resist further stretching of the wound coil.

According to another embodiment or aspect of the present invention, an embolic coil is provided with a wound coil having a plurality of turns defining a lumen. A headpiece is positioned at the proximal portion of the wound coil and an endcap is positioned at the distal portion of the wound coil. The embolic coil further includes a stretch resistant member at least partially received within the lumen and having a proximal end, a distal end, an enlarged portion, and an anchored portion. The anchored portion is fixedly attached to the wound coil, the headpiece, or the endcap. A restrictor member is at least partially received within the lumen and defines an aperture smaller than the enlarged portion. A portion of the stretch resistant member is movable through the aperture to allow stretching of the wound coil until the enlarged portion engages the restrictor member to resist further stretching of the wound coil.

According to yet another embodiment or aspect of the present invention, an embolic coil is provided with a wound coil having a plurality of major turns defining a lumen. The embolic coil further includes a stretch resistant member at least partially received within the lumen and having a proximal end, a distal end, and an enlarged portion. A minor turn of wound coil defines an aperture smaller than the enlarged portion to define a restrictor member. A portion of the stretch resistant member is movable through the aperture to allow stretching of the wound coil until the enlarged portion engages the minor turn and resists further stretching of the wound coil. In one embodiment, the stretch resistant member is separate from the remainder of the embolic coil and allowed to "free float" within the lumen. In another embodiment, one portion of the stretch resistant member is fixedly attached to the wound coil, a headpiece, or an endcap to provide a proximally or distally anchored stretch resistant member.

BRIEF DESCRIPTION OF THE DRAWINGS

FIG. 1 is a cross sectional view of an embolic coil having a free-floating stretch resistant member according to an aspect of the present invention, in a relaxed or un-stretched condition;

FIG. 2 is a cross sectional view of the embolic coil of FIG. 1, in a stretched condition;

FIG. 3 is a cross sectional view of an embolic coil having a proximally anchored stretch resistant member according to an aspect of the present invention;

FIG. 4 is a cross sectional view of an embolic coil having a distally anchored stretch resistant member according to an aspect of the present invention;

FIG. 5 is a cross sectional view of another embodiment of an embolic coil having a free-floating stretch resistant member; and FIG. 6 is a cross sectional view of another embodiment of an embolic coil having a proximally anchored stretch resistant member.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIGS. 1 and 2 illustrate an embolic coil 10 according to an aspect of the present invention. The embolic coil 10 includes a wound coil 12 comprised of a plurality of turns 14 defining a central lumen 16. The wound coil 12 is illustrated as a substantially uniform helical coil, but may take virtually any form, such as a coil having a varying pitch or random shape configuration. The wound coil 12 may be comprised of any material, but it may be preferred to use a radiopaque material, such as platinum, or to at least provide the wound coil 12 with a radiopaque layer or markers to improve traceability within a body vessel.

The wound coil 12 extends from a proximal portion 18 to a distal portion 20 and, in the illustrated embodiment, is bounded by a headpiece 22 positioned at the proximal portion 18 and an endcap 24 positioned at the distal portion 20. The means for fixing the headpiece 22 and the endcap 24 to the wound coil 12 will depend on the materials used for each, but suitable means may include welding, crimping, adhesion, bonding, and press fitting. The endcap 24 may be rounded or generally hemispherical to provide the embolic coil 10 with an atraumatic tip that prevents the device from puncturing a body vessel or target site during and after delivery. The headpiece 22 is adapted to interact with a delivery device, such as a catheter, during deployment of the embolic coil 10 to a target site, so the structure will vary according to the nature of the delivery device.

A free-floating stretch resistant member 26 is at least partially received within the lumen 16 of the wound coil 12. The term "free-floating" refers to the fact that the stretch resistant member 26 is in no way fixedly attached to the wound coil 12 or any other component of the embolic coil 10. In the embodiment of FIGS. 1 and 2, the stretch resistant member 26 has a generally dumbbell-shaped configuration with a proximal enlarged portion 28 and a distal enlarged portion 30 joined by an elongated, filamentary intermediate portion 32. While the proximal enlarged portion 28 is illustrated at the proximal end of the stretch resistant member 26 and the distal enlarged portion 30 is illustrated at the distal end of the stretch resistant member 26, they may be spaced away from the ends. The enlarged portions 28 and 30 are preferably identical spheres, as shown in FIGS. 1 and 2, but they may be differently sized and/or shaped without departing from the scope of the present invention. The enlarged portions 28 and 30 are larger than the intermediate portion 32, but they are sized to fit within the lumen 16 of the wound coil 12 for axial movement therethrough until the wound coil 12 reaches the stretched condition of FIG. 2, taking into account the reduced diameter of the lumen 16 once the wound coil 12 begins to stretch.

The stretch resistant member 26 is preferably comprised of a relatively flexible material that is substantially non-ductile when subjected to the forces associated with stretching the wound coil 12. Suitable materials include metals, such as but not limited to stainless steel, platinum, and nitinol and other metallic alloys, and polymers such as but not limited to polyethylene terephthalate (PET) or other polyesters. It is also within the scope of the present invention to provide a composite stretch resistant member, having a polymeric intermediate portion 32 and metallic enlarged portions 28 and 30, for example. The flexibility and ductility of the stretch resistant member 26 will depend in part on the material composition, with more rigid materials, such as stainless steel and austenitic nitinol, being preferred for applications requiring less flexibility and more flexible materials, such as PET and martensitic nitinol, being preferred for applications requiring more flexibility.

The stretch resistant member 26 may be formed as a unitary piece or may be provided in multiple parts, for example with one or both of the enlarged portions 28 and 30 being separate from and joinable to the intermediate portion 32. If provided in multiple parts, the means for joining the intermediate portion 32 and the enlarged portions 28 and 30 will vary according to the materials used for each. The component parts of a metallic stretch resistant member may be joined by welding, crimping, or other known means, while the component parts of a polymeric stretch resistant member may be joined by bonding, adhesion, or other known means The total length "i" of the stretch resistant member intermediate portion 32 is less than the maximum stretched length of the wound coil 12 to limit the available degree of stretching, as will be described in greater detail herein, and is preferably less than the length of the wound coil 12 in the relaxed or un-stretched condition of FIG. 1. Depending on the length and material composition of the stretch resistant member 26, slack in the intermediate portion 32 may cause it to assume a drooped condition (not illustrated) when the embolic coil 10 is in the relaxed condition of FIG. 1, but this will not affect the operation of the device.

In the embodiment of FIGS. 1 and 2 for example, the intermediate portion 32 of the stretch resistant member 26 is movably received by a proximal restrictor member 34 and a distal restrictor member 36. The restrictor members 34 and 36 are spaced from each other and positioned between the enlarged portions 28 and 30. In the illustration of the embodiment of FIGS. 1 and 2, the restrictor members 34 and 36 are generally tubular members fixedly attached to an interior circumference "c" of at least one of the turns 14 of the wound coil 12. Each restrictor member defines an aperture 38, 40 sufficiently sized to receive the intermediate portion 32 of the stretch resistant member 26. Preferably, the restrictor members 34 and 36 are sufficiently strong to resist being crushed or otherwise deformed by the tendency of the associated turns to stretch and radially contract, because causing the restrictor members to so contact the stretch resistant member intermediate portion 26 may adversely affect the expected operation of the embolic coil 10.

The aperture 38 of the proximal restrictor member 34 is smaller than the proximal enlarged portion 28, and the aperture 40 of the distal restrictor member 36 is smaller than the distal enlarged portion 30. Hence, it will be seen that the stretch resistant member 26 is allowed to move axially through the lumen 16, with the apertures 38 and 40 guiding the intermediate portion 32, but movement of the enlarged portions 28 and 30 into engagement with the restrictor members 34 and 36, respectively (FIG. 2), limits the range of movement between the stretch resistant member 26 and the coil turns 14.

The term "aperture" is to be construed broadly and is not limited to fully bounded openings, but to any opening adapted to allow movement of the stretch resistant member intermediate portion without allowing passage of the associated enlarged portion. For example, a C-shaped restrictor member (not illustrated) may be incorporated into embolic coils according to the present invention. Another suitable configuration is a two-piece restrictor member having an arcuate, U-shaped lower piece and an inverted U-shaped upper piece (not illustrated) in touching or spaced relationship to each other. Regardless of the specific shape of the aperture, the restrictor member is preferably adapted to prevent the stretch resistant member intermediate portion 32 from escaping from the aperture, which may affect the operation of the stretch resistant member 26. As the embolic coil 10 and the stretch resistant member 26 are intended to be flexible in multiple bending planes, an aperture 38, 40 provided as a fully bounded opening may be preferred to eliminate the risk of disengagement in any bending condition.

In addition to the tubular configuration of FIGS. 1 and 2, a generally annular restrictor member configuration may also be preferred. FIGS. 3 and 4 illustrate embolic coils 10a and 10b having a generally annular restrictor member 42 that is fixedly attached between adjacent turns 14 of the wound coil 12. It is also contemplated that the restrictor member 42 may be secured to only one of the turns 14, rather than two. The restrictor member 42 of FIGS. 3 and 4 has an aperture 44 functioning substantially the same as the apertures 38 and 40 of FIGS. 1 and 2. While only one restrictor member 42 is shown in FIGS. 3 and 4, it will be appreciated that a pair of annular restrictor members 42 may be incorporated into the embodiment of FIGS. 1 and 2 without departing from the scope of the present invention. Furthermore, according to another embodiment, the proximal and distal restrictor members may be different from each other, for example with one tubular restrictor member and one annular restrictor member.

The interaction between the stretch resistant member 26 and the restrictor members 34 and 36 regulates the stretching of the portion 46 of the wound coil 12 between the restrictor members 34 and 36, which portion is referred to herein as the restricted portion. In particular, the embolic coil 10 is allowed to elongate and stretch, which moves the restrictor members 34 and 36 along the intermediate portion 32 of the stretch resistant member 26 and increases the distance therebetween. Upon sufficient stretching, the proximal restrictor member 34 engages the proximal enlarged portion 28 and the distal restrictor member 36 engages the distal elongated portion 30 (FIG. 2) to resist or prevent further stretching. Hence, the total distance that the restricted portion 46 is allowed to stretch is equal to the difference between the length "i" of the stretch resistant member intermediate portion 32 and the initial distance "R" between the restrictor members 34 and 36 (FIG. 1).

It will be seen that the stretch resistant member 26 regulates the stretching of only the restricted portion 46, and the stretching of the remainder of the wound coil 12 is otherwise uninhibited. Therefore, the overall operation of the embolic coil 10 depends on a number of factors, including: (1) the ratio of the restricted portion 46 to the entire wound coil 12, (2) the total distance that the restricted portion 46 is allowed to stretch, and (3) the position of the restricted portion 46. The free-floating stretch resistant member 26 is particularly suited to a restricted portion 46 spaced from the proximal portion 18 and distal portion 20 of the wound coil 12, but alternative stretch-resistant members may be provided to achieve a restricted portion at the proximal or distal portions of the wound coil.

For example, FIG. 3 illustrates a proximally anchored stretch resistant member 26a. The stretch resistant member 26a includes an intermediate portion 32a and distal enlarged portion 30a according to the foregoing description, as well as an anchored portion 48. The anchored portion 48 is fixedly attached to a portion of the embolic coil 10a, such as the headpiece 22 (FIG. 3) or the proximal portion 18 of the wound coil 12 (shown in phantom in FIG. 3). The anchored portion 48 may be secured by any suitable means, including welding, crimping, adhesion, bonding, and the like.

The embolic coil 10a of FIG. 3 is illustrated with a generally annular restrictor member 42, but the restrictor member may take any of a number of forms, per the foregoing description, including the tubular configuration of FIGS. 1 and 2. The embolic coil 19a of FIG. 3 operates similarly to the embodiment of FIGS. 1 and 2, with the restricted portion 46a of the wound coil 12 being defined by the portion between the stretch resistant member anchored portion 48 and the restrictor member 42. In particular, the embolic coil 10a is allowed to elongate and stretch, which moves the restrictor member 42 along the intermediate portion 32a of the stretch resistant member 26a and increases the distance between the restrictor member 42 and the anchored portion 48. Upon sufficient stretching, the restrictor member 42 engages the enlarged portion 30a (not illustrated) to resist or prevent further stretching. Hence, the total distance that the restricted portion 46a is allowed to stretch is equal to the difference between the length "i" of the stretch resistant member intermediate portion 32a and the initial distance "R'" between the restrictor member 42 and the anchored portion 48 (FIG. 3).

As shown in phantom in FIG. 3, the anchored portion 48 may be fixedly attached to the wound coil 12 instead of the headpiece 22. In such an embodiment, the stretch resistant member 26a preferably includes a radially extending member 49 adapted to be welded, adhered, or otherwise fixedly secured to one or more of the coils 14 of the wound coil 12. For illustrative purposes, the radially extending member 49 is shown in FIG. 3 as a generally spherical structure, but it may be provided in any of a number of simple or complex shapes, including a cylindrical orientation or a "flower-petal" configuration with a plurality of angularly spaced radial projections. Alternatively, the wound spring 12 may be provided with at least one radially inwardly projecting member (not illustrated) adapted to be fixedly secured to the stretch resistant member 26a. Typically, a stretch resistant member 26a secured to the wound coil 12 will not be additionally secured to the headpiece 48, although it may be secured at both locations. As shown in phantom in FIG. 3, the length "i" of the intermediate portion 32a and the distance "R'" between the restrictor member 42 and the anchored portion 48 will be shorter than for a stretch resistant member 26a anchored to the headpiece 22.

FIG. 4 illustrates a distally anchored stretch resistant member 26b, which may be preferred for applications requiring regulation of the stretching of the wound coil distal portion 20. The embolic coil 10b includes a restrictor member 42 and a stretch resistant member 26b having an intermediate portion 32b, a proximal enlarged portion 28a, and an anchored portion 50. In contrast to the embodiment of FIG. 3, the anchored portion 50 is fixedly attached to a portion of the embolic coil 10b distal of the restrictor member 42 and the enlarged portion 28a, such as the endcap 24 (FIG. 4) or the distal portion 20 of the wound coil 12 (shown in phantom in FIG. 4) to define a distal restricted portion 46b. The anchored portion 50 may be secured by any suitable means, including welding, crimping, adhesion, bonding, and the like.

In use, the embolic coil 10b is allowed to elongate and stretch, which moves the restrictor member 42 along the intermediate portion 32b of the stretch resistant member 26b and increases the distance between the restrictor member 42 and the anchored portion 50. Upon sufficient stretching, the restrictor member 42 engages the enlarged portion 28a (not illustrated) to resist or prevent further stretching of the restricted portion 46b. Hence, as with the embodiment of FIG. 3, the total distance that the restricted portion 46b is allowed to stretch is equal to the difference between the length "i" of the stretch resistant member intermediate portion 32b and the initial distance "R''" between the restrictor member 42 and the anchored portion 50 (FIG. 4).

As shown in phantom in FIG. 4, the anchored portion 50 may be fixedly attached to the wound coil 12 instead of the endcap 24. In such an embodiment, the stretch resistant member 26b preferably includes a radially extending member 51, substantially similar to the radially extending member 49 of FIG. 3. Typically, a stretch resistant member 26b so secured will not be additionally secured to the endcap 24, although it may be secured at both locations. As shown in phantom in FIG. 4, the length "i" of the intermediate portion 32b and the distance "R''" between the restrictor member 42 and the anchored portion 50 will be shorter than for a stretch resistant member 26b anchored to the endcap 24.

While the restrictor members of FIGS. 1-4 are described as separate elements, the wound coil may be adapted to provide one or more restrictor member-like elements. For example, FIG. 5 illustrates an embolic coil 10c comprising a wound coil 52 having a plurality of major turns 54, corresponding generally to the coil turns 14 of FIGS. 1-4, and two sets of minor turns 56 and 58. While each set of minor turns 56 and 58 is illustrated as comprising two turns, they may also be provided as a single turn or as more than two turns or with differing numbers of turns. Minor turns 56 and 58 provide a passageway that is of reduced internal size, typically diameter, with respect to the internal size of the major turns 54.

The embolic coil 10c of FIG. 5 includes the free-floating stretch resistant member 26 of FIGS. 1 and 2. The minor turns 56 and 58 define apertures 60 and 62, respectively, sufficiently sized to receive the intermediate portion 32 of the stretch resistant member 26. The aperture 60 of the proximal minor turn 56 is smaller than the proximal enlarged portion 28 and the aperture 62 of the distal minor turn 58 is smaller than the distal enlarged portion 30. Hence, the stretch resistant member 26 is axially movable through the lumen 16, with the apertures 60 and 62 guiding the intermediate portion 32, and the enlarged portions 28 and 30 move into engagement with the minor turns 56 and 58, respectively (not illustrated), to limit the range of movement of the stretch resistant member 26 and perform a proximal/distal restrictor function.

The apertures 60 and 62 of the minor turns 56 and 58 typically can be larger than the apertures of FIGS. 1-4 relative to the rest of the device such as the enlarged portions, because the minor turns 56 and 58 may stretch and elongate, thereby decreasing the size of the apertures 60 and 62. If the apertures 60 and 62 are not sufficiently large, they may shrink to the point where they engage and grip the intermediate portion 32 of the stretch resistant member 26 (not illustrated), which may affect the intended operation of the stretch resistant member 26. Of course, this gripping action may be factored into the design of the embolic coil 10c, in which case it may be considered as an auxiliary or alternative stretch resistant feature.

Provided that the apertures 60 and 62 are sufficiently large to avoid gripping the stretch resistant member intermediate portion 32, the embolic coil 10c of FIG. 5 operates according to the foregoing description of the embodiment of FIGS. 1 and 2, with the minor turns 56 and 58 defining the restricted portion 46c of the wound coil 52 and engaging the enlarged portions 28 and 30, respectively, to prevent or resist stretching of the restricted portion 46c.

Just as the wound coil may be adapted to provide restrictor member-like elements similar to the restrictor members 34 and 36 of FIGS. 1 and 2, it may also be adapted to provide elements similar the restrictor member 42 of FIGS. 3 and 4. In particular, FIG. 6 illustrates an embolic coil 10d having a wound coil 64 comprised of major turns 66 and one set of minor turns 68. While two minor turns are illustrated, the stretch resisting function may be achieved by a single minor turn or more than two minor turns. The embolic coil 10d includes the proximally anchored stretch resistant member 26a of FIG. 3 and, except for the use of a minor turn 68 instead of a separate restrictor member 42, the embodiment of FIG. 6 operates identically to the embodiment of FIG. 3. It will be appreciated that the embodiment of FIG. 4 can similarly be modified by removing the restrictor member 42 and replacing it with a minor turn of the wound coil (not illustrated). As with the embodiments of FIGS. 3 and 4, the anchored portion 48 of the stretch-resistant member 26a may be secured to the wound coil 12 (shown in phantom in FIG. 6) instead of the headpiece 22 or the endcap 24.

Although the embolic coils of FIGS. 1-6 are shown as including only a single stretch resistant member, a single coil may include two or more stretch resistant members spaced along the length of its lumen. For example, an embolic coil may be provided with a proximally anchored stretch resistant member (FIGS. 3 and 6) and a distally anchored stretch resistant member (FIG. 4) at the ends of the wound coil, with a free-floating stretch resistant member (FIGS. 1, 2, and 5) spaced between the anchored stretch resistant members. This may be useful in providing various portions of the wound coil with different stretch and bending properties.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An embolic coil comprising:
   a plurality of substantially coaxial components including a radially external component, a radially internal component and radially intermediate components;
   a wound coil including a plurality of turns defining a lumen having a proximal end and a distal end, the wound coil being the radially external coaxial component;
   a free-floating stretch resistant member that is fixedly unattached to the wound coil while being at least partially received within the wound coil lumen, the free-floating stretch resistant member having a proximal end, a distal end, a proximal enlarged portion, and a distal enlarged portion, the stretch resistant member being the radially internal coaxial component, the lumen of the wound coil is larger than the proximal enlarged portion and than the distal enlarged portion whereby these proximal and distal enlarged portions are movable through the coil lumen and one or both of the proximal and distal ends of the wound coil extend beyond the respective enlarged portion of the stretch-resistant member;

proximal and distal restrictor members at least partially received within and fixedly attached to the lumen of the wound coil, the restrictor members being the radially intermediate coaxial components, wherein the proximal restrictor member defines an aperture smaller than the proximal enlarged portion of the stretch resistant member; and the distal restrictor member defines an aperture smaller than the distal enlarged portion of the stretch resistant member, the restrictor member apertures being substantially coaxial with the radially external, internal and intermediate components, a portion of the stretch resistant member is movable through the apertures to allow stretching of the wound coil during relative axial movement between the stretch resistant member and the restrictor member, the proximal enlarged portion of the stretch resistant member is adapted to engage the proximal restrictor member to resist stretching of the wound coil, and the distal enlarged portion of the stretch resistant member is adapted to engage the distal restrictor member to resist stretching of the wound coil.

2. The embolic coil of claim 1, wherein said restrictor members are intermediate the enlarged portions of the stretch resistant member.

3. The embolic coil of claim 2, wherein said proximal enlarged portion is positioned at the proximal end of the stretch resistant member and said distal enlarged portion is positioned at the distal end of the stretch resistant member.

4. The embolic coil of claim 1, wherein at least one of said restrictor members comprises a generally tubular member fixedly attached to an interior circumference of at least one of the turns of the wound coil.

5. The embolic coil of claim 1, wherein at least one of said restrictor members comprises a generally annular member fixedly attached between adjacent turns of the wound coil.

6. The embolic coil of claim 1, wherein said stretch resistant member is substantially comprised of a metallic material.

7. The embolic coil of claim 1, wherein said stretch resistant member is substantially comprised of a polymeric material.

8. An embolic coil comprising:
a plurality of substantially coaxial components including a radially external component, a radially internal component and a radially intermediate component;
a wound coil including a plurality of turns defining a lumen having a proximal end and a distal end, the wound coil being the radially external coaxial component;
a headpiece positioned at a proximal portion of the wound coil;
an endcap positioned at a distal portion of the wound coil;
a stretch resistant member that is fixedly unattached to at least one of the proximal and distal ends of the wound coil while being at least partially received within the wound coil lumen, the stretch-resistant member having a proximal end, a distal end, an enlarged portion, and an anchored portion fixedly attached to the wound coil, the headpiece or the endcap, the stretch resistant member being the radially internal coaxial component;
the lumen of the wound coil is larger than the enlarged portion whereby the enlarged portion is movable through the coil lumen and the wound coil endcap extends beyond the enlarged portion of the stretch-resistant member; and a restrictor member at least partially received within and fixedly attached to the lumen, the restrictor member being the radially intermediate coaxial component, wherein the restrictor member defines an aperture smaller than the enlarged portion of the stretch resistant member, a portion of the stretch resistant member is movable through the aperture to allow stretching of the wound coil during relative axial movement of the stretch resistant member through the restrictor member, and the enlarged portion of the stretch resistant member is adapted to engage the restrictor member to resist stretching of the wound coil.

9. The embolic coil of claim 8, wherein said enlarged portion is positioned distally of the anchored portion.

10. The embolic coil of claim 8, wherein said enlarged portion is positioned proximally of the anchored portion.

11. The embolic coil of claim 8, wherein said restrictor member comprises a generally tubular member fixedly attached to an interior circumference of at least one of the turns of the wound coil.

12. The embolic coil of claim 8, wherein said restrictor member comprises a generally annular member fixedly attached between adjacent turns of the wound coil.

13. The embolic coil of claim 8, wherein said stretch resistant member is substantially comprised of a metallic material.

14. The embolic coil of claim 8, wherein said stretch resistant member is substantially comprised of a polymeric material.

15. An embolic coil comprising:
a plurality of substantially coaxial components including a radially external component, a radially internal component and a radially intermediate component;
a wound coil including a plurality of major turns defining a lumen having a proximal end and a distal end, the wound coil being the radially eternal coaxial component;
a stretch resistant member that is fixedly unattached to the wound coil while being at least partially received within the wound coil lumen, the stretch-resistant member having a proximal end, a distal end, and a first enlarged portion, the stretch resistant member being the radially internal axial component, the lumen of the wound coil is larger than the first enlarged portion whereby same is movable through the coil lumen and one or both of the proximal and distal ends of the wound coil extend beyond the first enlarged portion of the stretch-resistant member; and
the wound coil includes a first minor turn defining an aperture smaller than the first enlarged portion of the stretch resistant member, the first minor turn being the radially intermediate component, a portion of the stretch resistant member is movable through the aperture to allow stretching of the wound coil during relative axial movement between the stretch resistant member and the first minor turn, and the first enlarged portion of the stretch resistant member is adapted to engage the minor turn to resist stretching of the wound coil.

16. The embolic coil of claim 15, further comprising a headpiece positioned at a proximal portion of the wound coil, an endcap positioned at a distal portion of the wound coil, and an anchored portion of the stretch resistant member fixedly attached to the wound coil, the headpiece, or the endcap.

17. The embolic coil of claim 16, wherein said first enlarged portion is positioned distally of the anchored portion.

18. The embolic coil of claim 16, wherein said first enlarged portion is positioned proximally of the anchored portion.

19. The embolic coil of claim 15, further comprising a second enlarged portion of the stretch resistant member and a second minor turn spaced from the first minor turn and defining an aperture smaller than the second enlarged portion, the second minor turn being a second radially intermediate component, wherein a portion of the stretch resistant member is movable through the apertures of the minor turns to allow stretching of the wound coil during relative axial movement between the stretch resistant member and the second minor turn, and the second enlarged portion of the stretch resistant member is adapted to engage the second minor turn to resist stretching of the wound coil.

20. The embolic coil of claim 19, wherein said minor turns are intermediate the enlarged portions of the stretch resistant member.

21. The embolic coil of claim 20, wherein said first enlarged portion is positioned at one of the proximal and distal ends of the stretch resistant member and said second enlarged portion is positioned at the other end of the stretch resistant member.

22. The embolic coil of claim 15, wherein said stretch resistant member is substantially comprised of a metallic material.

23. The embolic coil of claim 15, wherein said stretch resistant member is substantially comprised of a polymeric material.

* * * * *